United States Patent [19]

Ulrich et al.

[11] Patent Number: 4,621,093
[45] Date of Patent: * Nov. 4, 1986

[54] VASO-DILATING AND CORONARY ACTIVE 4-NITROPHENYL-TETRAHYDROPYRIDINES

[75] Inventors: Rosentreter Ulrich; Günter Thomas; Andreas Knorr, all of Wuppertal, Fed. Rep. of Germany

[73] Assignee: Bayer Aktiengesellschaft, Leverkusen, Fed. Rep. of Germany

[*] Notice: The portion of the term of this patent subsequent to Feb. 4, 2003 has been disclaimed.

[21] Appl. No.: 720,668

[22] Filed: Apr. 8, 1985

[30] Foreign Application Priority Data

Apr. 19, 1984 [DE] Fed. Rep. of Germany ....... 3414801

[51] Int. Cl.$^4$ ................ A61K 31/455; C07D 211/78; C07D 211/70
[52] U.S. Cl. .................................... 514/355; 514/356; 546/321; 546/322; 546/316; 546/286
[58] Field of Search ............... 546/321, 316, 322, 286; 514/356, 355

[56] References Cited

U.S. PATENT DOCUMENTS 4,532,248 7/1985 Franckowiak et al. ............. 514/352

OTHER PUBLICATIONS

Bossert, F. et al. "4-Aryldihydropyridines" Angew. Chem. Int. Ed. Engl. 20 (1981) pp. 762-769.

Primary Examiner—Henry H. Jiles
Assistant Examiner—Dale A. Bjorkman
Attorney, Agent, or Firm—Sprung, Horn, Kramer & Woods

[57] ABSTRACT 4-(Nitrophenyl)-1,2,3,4-tetrahydropyridines of the formula

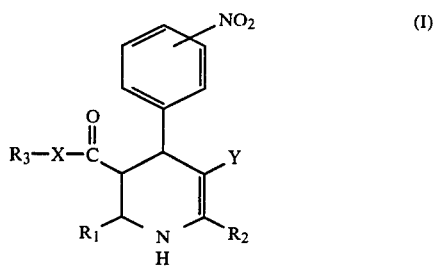

in which $R_1$ and $R_2$ are identical or different and each represent hydrogen, phenyl or a straight-chain or branched alkyl radical which is optionally substituted by halogen or alkoxy, $R_3$ represents a straight-chain or branched alkyl radical which is optionally substituted by alkoxy, halogen, alkylamino or aryl, X represents a single bond, an oxygen atom, a sulphur atom or the NH group and Y denotes either the nitrile group or the radical

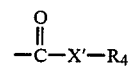

wherein X' corresponds to the definition of X and can either be identical to X or different from X, and $R_4$ corresponds to the definition of $R_3$ and can be either identical to $R_3$ or different from $R_3$, or physiologically acceptable salts thereof, which are active on the circulation system, for example as vasodilators.

12 Claims, No Drawings

VASO-DILATING AND CORONARY ACTIVE 4-NITROPHENYL-TETRAHYDROPYRIDINES

The new invention relates to new 4-nitrophenyltetrahydropyridines, a process for their preparation and their use as medicaments, in particular as agents which influence the circulation.

The present invention relates to new 4-(nitrophenyl)-1,2,3,4-tetrahydropyridines of the general formula (I)

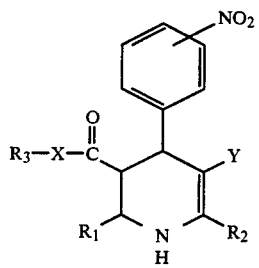

in which
- $R_1$ and $R_2$ are identical or different and each represent hydrogen, phenyl or a straight-chain or branched alkyl radical which is optionally substituted by halogen or alkoxy,
- $R_3$ represents a straight-chain or branched alkyl radical which is optionally substituted by alkoxy, halogen, alkylamino or aryl,
- X represents a single bond, an oxygen atom, a sulphur atom or the NH group and
- Y denotes either the nitrile group or the radical

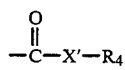

wherein
- X' corresponds to the definition of X and can either be identical to X or different from X, and
- $R_4$ corresponds to the definition of $R_3$ and can be either identical to $R_3$ or different from $R_3$, and their physiologically acceptable salts.

It has been found that the compounds of the formula (I) according to the invention are obtained when dihydropyridine compounds of the general formula (II)

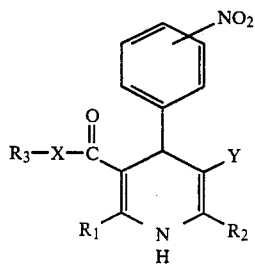

in which $R_1$, $R_2$, $R_3$, Y and X have the abovementioned meaning, are reduced in a strongly acid reaction medium by means of suitable hydride donors.

The 4-(nitrophenyl)-1,2,3,4-tetrahydro-Pyridine derivatives according to the invention have useful pharmacological properties. On the basis of their action which influences the circulation, they can be used as anti-hypertensive agents, as peripheral and cerebral vasodilators and as coronary therapeutics, and are thus to be regarded as an enrichment of pharmacy.

The preparation of the compounds according to the invention can be represented by the following equation, in which dimethyl 2,6-dimethyl-4-(2-nitrophenyl)-1,2,3,4-tetrahydropyridine-3,5-dicarboxylate is chosen as an example:

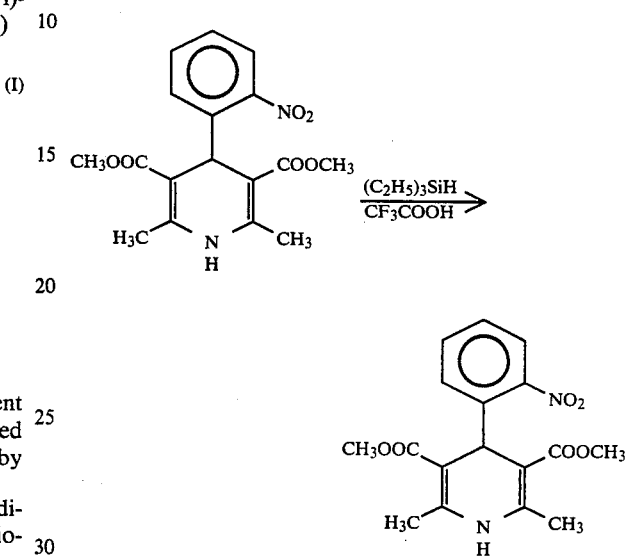

According to this process, the reduction of the 1,4-dihydropyridines employed is carried out in a strongly acid reaction medium.

Preferred strongly acid reaction media which may be mentioned are: trifluoroacetic acid, mixtures of trifluoroacetic acid and acetic acid, methylene chloride, chloroform, benzene, toluene, 1,2-dichloroethane, dioxane, tetrahydrofuran, nitromethane and acetonitrile, mixtures of sulphuric acid and glacial acetic acid, solutions of methanesulphonic acid or p-toluenesulphonic acid in methylene chloride, chloroform, benzene, toluene, 1,2-dichloroethane, dioxane, tetrahydrofuran, nitromethane and acetonitrile, and mixtures of these reaction media.

The reduction is carried out by addition of 1 to 2 equivalents of a hydride donor, such as, for example, triethylsilane, triphenylsilane, tributyl-tin hydride, sodium cyanoborohydride, 1,4-dihydronaphthalene or 1,4-cyclohexadiene.

The reaction temperature can be widely varied, but the reaction is preferably carried out between 0° C. and 50° C.

Preferably, in the general formulae (I) and (II),
- $R_1$ and $R_2$ represent hydrogen, phenyl or a straight-chain or branched alkyl radical which has up to 4 carbon atoms and can be substituted by fluorine or chlorine,
- $R_3$ represents an alkyl radical which has up to 10 carbon atoms and is optionally substituted by alkoxy with 1 to 4 carbon atoms, fluorine, chlorine, phenyl or alkylamino with in each case 1 to 4 carbon atoms in the alkyl groups,
- X represents a single bond, an oxygen atom or a sulphur atom and
- Y represents either the nitrile group or the radical

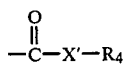

wherein
X' corresponds to the definition of X and can be either identical to X or different from X, and
R$_4$ corresponds to the definition of R$_3$ and can be either identical to R$_3$ or different from R$_3$.

Compounds of the general formula (I) which are of particular interest are those in which R$_1$ and R$_2$ each represent alkyl with 1 to 4 carbon atoms, R$_3$ represents a straight-chain or branched alkyl radical which has up to 10 carbon atoms and is optionally interrupted by oxygen in the chain or substituted by fluorine or chlorine, X represents a single bond, an oxygen atom or the NH group and Y represents a nitrile group or the radical —CO—X'—R$_4$ wherein X' and R$_4$ in each case have the meaning of X and R$_3$ and can be identical to or different from these radicals.

The 1,4-dihydropyridine derivatives of the general formula (II) used as starting substances are known from the literature, or they can be prepared by methods which are known from the literature (compare, for example, K. Eisner and J. Kuthan, Chem. Rev. 71, 1 (1972); and DOS (German Published Specification) 2,658,804).

The following compounds may be mentioned as examples, in addition to the embodiment examples: dipropyl t-2,6-dimethyl-t-4-(2-nitrophenyl)-1,2,3,4-tetrahydropyridine-r-3,5-dicarboxylate, dipropyl t-2,6-dimethyl-t-4-(3-nitrophenyl)-1,2,3,4-tetrahydropyridine-r-3,5-dicarboxylate, di-(2-methoxyethyl) t-2,6-dimethyl-t-4-(2-nitrophenyl)-1,2,3,4-tetrahydropyridine-r-3,5-dicarboxylate, di-(2-methoxyethyl) t-2,6-dimethyl-t-4-(3-nitrophenyl)-1,2,3,4-tetrahydropyridine-r-3,5-dicarboxylate, 3-isopropyl-5-methyl t-2,6-dimethyl-t-4-(3-nitrophenyl)-1,2,3,4-tetrahydropyridine-r-3-carboxylate, 3-ethyl-5-methyl t-2,6-dimethyl-t-4-(3-nitrophenyl)-1,2,3,4-tetrahydropyridine-r-3-carboxylate, 3-isopropyl-5-(2-methoxyethyl) t-2,6-dimethyl-t-4-(3-nitrophenyl)-1,2,3,4-tetrahydropyridine-r-3-carboxylate.

Depending on the nature of the radicals R$_1$, R$_2$, R$_3$, X and Y, the compounds according to the invention have at least three centers of asymmetry and can therefore occur in several stereoisomeric forms. The present invention relates both to the antipodes and to the racemic forms as well as to the diastereomer mixtures. The racemic forms and also the diastereomers can be resolved into the stereoisomerically uniform constituents in a known manner (compare, for example, E. L. Eliel, Stereochemistry of Carbon Compounds, McGraw Hill, 1962).

The new compounds have a broad and diverse pharmacological action spectrum.

In detail, it has been possible to demonstrate the following main actions in animal experiments:

1. On parenteral, oral and perlingual administration, the compounds produce a distinct and long-lasting dilation of the coronary vessels. This action on the coronary vessels in intensified by a simultaneous nitrite-like effect of reducing the load on the heart. They influence or modify heart metabolism in the sense of energy saving.
2. The excitability of the stimulus formation and excitation conduction system within the heart is lowered, so that an antifibrilation action which can be demonstrated at therapeutic doses results.
3. The tone of the smooth muscle of the vessels is greatly reduced under the action of the compound. This vasospasmolytic action can take place in the entire vascular system or can manifest itself more or less isolated in circumscribed vascular regions (such as, for example, the central nervous system). The compounds are therefore particularly suitable as cerebral therapeutics.
4. The compounds lower the blood pressure of normotensive and hypertensive animals and can thus be used as antihypertensive agents.
5. The compounds have powerful muscular-spasmolytic actions, which manifest themselves on the smooth muscle of the stomach, gastrointestinal tract, urogenital tract and respiratory system.

On the basis of these properties, the compounds according to the invention are particularly suitable for the prophylaxis and therapy of acute and chronic ischaemic heart diseases in the broadest sense, for the therapy of high blood pressure and for the treatment of disorders in cerebral and peripheral circulation.

The new active compounds can be converted in a known manner into the customary formulations, such as tablets, capsules, dragees, pills, granules, aerosols, syrups, emulsions, suspensions and solutions, using inert, non-toxic pharmaceutically suitable excipients or solvents. The therapeutically active compound should in each case be present in a concentration of about 0.5 to 90% by weight of the total mixture, that is to say in amounts suffice to achieve the indicated dosage range.

The formulations are prepared, for example, by extending the active compounds with solvents and/or excipients, if appropriate using emulsifiers and/or dispersing agents and, for example in the case of water being employed as the diluent, organic solvents can be used as auxiliary solvents if appropriate.

Examples of auxiliary substances which may be mentioned are: water, non-toxic organic solvents, such as paraffins (for example petroleum fractions), vegetable oils (for example groundnut/sesame oil), alcohols (for example ethyl alcohol and glycerol) and glycols (for example propylene glycol and polyethylene glycol), solid excipients, such as, for example, natural rock powders (for example kaolins, aluminas, talc and chalk), synthetic rock powders (for example highly disperse silicic acid and silicates), sugars (for example canesugar, lactose and glucose), emulsifiers (for example polyoxyethylene fatty acid esters, polyoxyethylene fatty alcohol ethers, alkylsulphonates and arylsulphonates), dispersing agents (for example lignin sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, in particular perlingually or intravenously. In the case of oral use, tablets can of course also contain, in addition to the excipients mentioned, additives, such as sodium citrate, calcium carbonate and dicalcium phosphate, together with various further substances, such as starch, preferably potato starch, gelatin and the like. Furthermore, lubricants, such as magnesium stearate, sodium lauryl-sulphate and talc, can be used conjointly for tablet-making. In the case of aqueous suspensions and/or elixiers intended for oral use, the active compounds can be mixed with various flavour-improving agents or dyestuffs, in addition to the abovementioned auxiliaries.

In the case of parenteral use, solutions of the active compounds can be employed, using suitable liquid excipients.

In general, it has proved advantageous, in the case of intravenous administration, to administer amounts of about 0.001 to 10 mg/kg, preferably 0.05 to 5 mg/kg of body weight daily to achieve effective results, whilst in the case of oral administration the dosage is about 0.05 to 20 mg/kg, preferably 0.5 to 5 mg/kg of body weight daily.

Nevertheless, it can at times be necessary to deviate from the amounts mentioned, and in particular to do so as a function of the body weight of the experimental animal or of the nature of the administration route, but also because of the species of animal and its individual behavior towards the medicament or the nature of its formulation and the time or interval at which administration takes place. Thus, it may suffice in some cases to manage with less than the abovementioned minimum amount, while in other cases the upper limit mentioned must be exceeded.

EMBODIMENT EXAMPLES

EXAMPLE 1

Dimethyl t-2,6-dimethyl-t-4-(2-nitrophenyl)-1,2,3,4-tetrahydropyridine-r-3,5-dicarboxylate 10 g (29 mmole) of dimethyl 2,6-dimethyl-4-(2-nitrophenyl)-1,4-dihydropyridine-3,5-dicarboxylate are dissolved in 100 ml of trifluoroacetic acid, and 5.6 ml (36.1 mmole) of triethylsilane are added. The reaction mixture is then stirred at 50° C. for 15 minutes. Thereafter, it is diluted with a large amount of water and extracted twice with ethyl acetate. The combined ethyl acetate phases are washed 3 times with saturated bicarbonate solution, dried with magnesium sulphate and evaporated. The residue thus obtained crystallizes from ether. Yield: 6.6 g (66% of theory); melting point: 157°–160° C.

The examples listed in the following Table 1 were prepared analogously to Example 1:

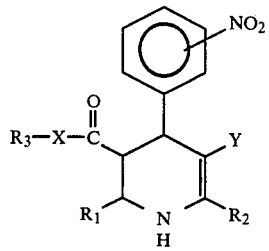

TABLE 1

| Example No. | $R_1$ | $R_2$ | $R_3$ | Aryl | X | Y | Melting point (°C.) | Yield in % of theory |
|---|---|---|---|---|---|---|---|---|
| 2 | $C_2H_5$ | $C_2H_5$ | $CH_3$ | 2-$NO_2$-$C_6H_4$ | O | $COOCH_3$ | 67–73 | 58 |
| 3 | $CH_3$ | $CH_3$ | $C_2H_5$ | 2-$NO_2$-$C_6H_4$ | O | $COOC_2H_5$ | 84–87 | 84 |
| 4 | $CH_3$ | $CH_3$ | $C_2H_5$ | 3-$NO_2$-$C_6H_4$ | O | $COOC_2H_5$ | 110–114 | 73 |
| 5 | $CH_3$ | $CH_3$ | $CH_3$ | 2-$NO_2$-$C_6H_4$ | Single bond | $\underset{\parallel}{C}(=O)-CH_3$ | 175–180 | 64 |

TABLE 1-continued

| Example No. | $R_1$ | $R_2$ | $R_3$ | | X | Y | Melting point (°C.) | Yield in % of theory |
|---|---|---|---|---|---|---|---|---|
| 6 | $CH_3$ | $CH_3$ | $CH_3$ | 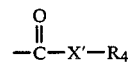 | O | CN | 202–204 | 63 |
| 7 | $CH_3$ | $CH_3$ | $C_2H_5$ | 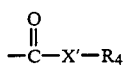 | O | $COOC_2H_5$ | 120 | 86 |

It will be understood that the specification and examples are illustrative but not limitative of the present invention and that other embodiments within the spirit and scope of the invention will suggest themselves to those skilled in the art.

We claim:

1. A 4-(nitrophenyl)-1,2,3,4-tetrahydropyridine of the formula

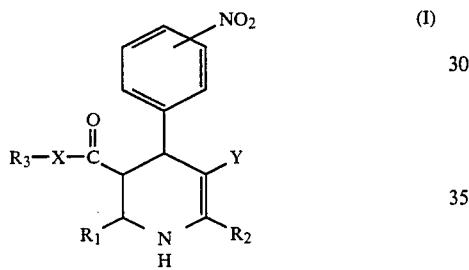

in which $R_1$ and $R_2$ are identical or different and each represent hydrogen, phenyl or a straight-chain or branched alkyl radical which is optionally substituted by halogen or alkoxy, $R_3$ represents a straight-chain or branched alkyl radical which is optionally substituted by alkoxy, halogen, alkylamino or aryl, X represents a single bond, an oxygen atom, a sulphur atom or the NH group and Y denotes the radical $$-\overset{O}{\underset{\|}{C}}-X'-R_4$$

wherein

X' corresponds to the definition of X and can either be identical to X or different from X, and $R_4$ corresponds to the definition of $R_3$ and can be either identical to $R_3$ or different from $R_3$, or a physiologically acceptable salt thereof.

2. A compound or salt according to claim 1, in which $R_1$ and $R_2$ represent hydrogen, phenyl or a straight-chain or branched alkyl radical which has up to 4 carbon atoms and can be substituted by fluorine or chlorine, $R_3$ represents an alkyl radical which has up to 10 carbon atoms and is optionally substituted by alkoxy with 1 to 4 carbon atoms, fluorine, chlorine, phenyl or alkylamino with in each case 1 to 4 carbon atoms in the alkyl groups, X represents a single bond, an oxygen atom or a sulphur atom and Y represents the radical $$-\overset{O}{\underset{\|}{C}}-X'-R_4$$

wherein

X' corresponds to the definition of X and can be either identical to X or different from X, and $R_4$ corresponds to the definition of $R_3$ and can be either identical to $R_3$ or different from $R_3$.

3. A compound or salt according to claim 1, in which $R_1$ and $R_2$ each represent alkyl with 1 to 4 carbon atoms, $R_3$ represents a straight-chain or branched alkyl radical which has up to 10 carbon atoms and is optionally interrupted by oxygen in the chain or substituted by fluorine or chlorine, X represents a single bond, an oxygen atom or the NH group and Y represents the radical $-CO-X'-R_4$ wherein X' and $R_4$ in each case have the meaning of X and $R_3$ and can be identical to or different from these radicals.

4. A compound according to claim 1, wherein such compound is dimethyl 2,6-dimethyl-4-(2-nitrophenyl)-1,2,3,4-tetrahydropyridine-3,5-dicarboxylate of the formula

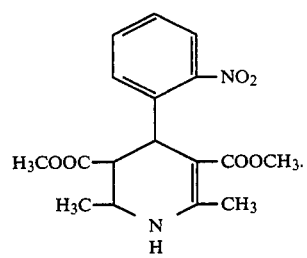

5. A compound according to claim 1, wherein such compound is dimethyl 2,6-diethyl-4-(3-nitrophenyl)-

1,2,3,4-tetrahydropyridine-3,5-dicarboxylate of the formula

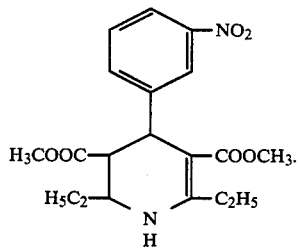

6. A compound according to claim 1, wherein such compound is diethyl 2,6-dimethyl-4-(3-nitrophenyl)-1,2,3,4-tetrahydropyridine-3,5-dicarboxylate of the formula

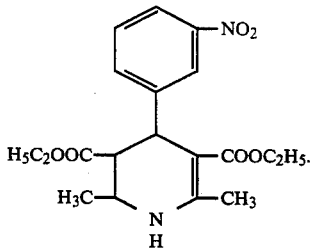

7. A compound according to claim 1, wherein such compound is dimethyl 2,6-dimethyl-4-(3-nitrophenyl)-1,2,3,4-tetrahydropyridine-3,5-dicarboxylate of the formula

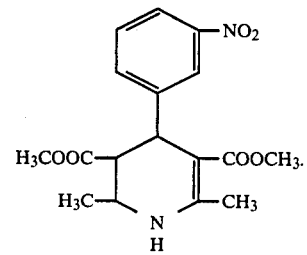

8. A compound according to claim 1, wheren such compound is diethyl 2,6-dimethyl-4-(2-nitrophenyl)-1,2,3,4-tetrahydropyridine-3,5-dicarboxylate of the formula

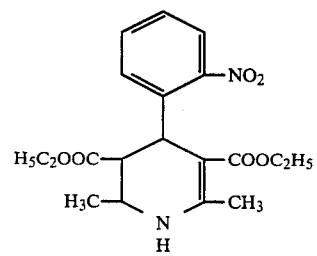

9. A composition exhibiting a nitrite-like effect of reducing the load on the heart, antifibrillation action, vasospasmolytic action and smooth muscle spasmolytic action comprising an amount effective therefor of a compound or salt according to claim 1 in admixture with a diluent.

10. A unit dose of a composition according to claim 9 in the form of a tablet, capsule or ampule.

11. A method of producing in a patient in need thereof a nitrite-like effect of reducing the load on the heart, antifibrillation action, vasospasmolytic action and smooth muscle spasmolytic action which comprises administering to such patient an amount effective therefor of a compound or salt according to claim 1.

12. The method according to claim 11, wherein such compound is
dimethyl 2,6-dimethyl-4-(2-nitrophenyl)-1,2,3,4-tetrahydropyridine-3,5-dicarboxylate,
dimethyl 2,6-diethyl-4-(3-nitrophenyl)-1,2,3,4-tetrahydropyridine-3,5-dicarboxylate,
diethyl 2,6-dimethyl-4-(3-nitrophenyl)-1,2,3,4-tetrahydropyridine-3,5-dicarboxylate,
dimethyl 2,6-dimethyl-4-(3-nitrophenyl)-1,2,3,4-tetrahydropyridine-3,5-dicarboxylate or
diethyl 2,6-dimethyl-4-(2-nitrophenyl)-1,2,3,4-tetrahydropyridine-3,5-dicarboxylate,
or a physiologically acceptable salt thereof.

* * * * *

UNITED STATES PATENT AND TRADEMARK OFFICE
CERTIFICATE OF CORRECTION

PATENT NO. : 4,621,093

DATED : November 4, 1986

INVENTOR(S) : Rosentreter Ulrich, et al.

It is certified that error appears in the above-identified patent and that said Letters Patent is hereby corrected as shown below:

Title Page, No. 75 "Inventors", Delete "Cünter" and substitute
line 1 --Günter--

Signed and Sealed this

Twenty-fourth Day of March, 1987

Attest:

DONALD J. QUIGG

Attesting Officer

Commissioner of Patents and Trademarks